United States Patent [19]

Fruchey et al.

[11] Patent Number: 4,529,550
[45] Date of Patent: Jul. 16, 1985

[54] HYDROLYSIS OF ANHYDRIDE IN THE PRODUCTION OF $C_5$-$C_9$ SATURATED ALIPHATIC MONOCARBOXYLIC ACIDS

[75] Inventors: Olan S. Fruchey; James S. Alder, both of Corpus Christi, Tex.

[73] Assignee: Celanese Corporation, New York, N.Y.

[21] Appl. No.: 458,423

[22] Filed: Jan. 17, 1983

[51] Int. Cl.$^3$ .................. C07C 51/235; C07C 53/126
[52] U.S. Cl. ..................................... 260/413; 260/546; 562/531; 562/606; 562/607; 562/608; 260/419
[58] Field of Search ............... 260/413 N, 546, 413 R, 260/419; 562/608, 531, 606, 607

[56] References Cited

U.S. PATENT DOCUMENTS 2,355,140  8/1944  Bludworth ........................ 562/531

FOREIGN PATENT DOCUMENTS 52-33614  3/1977  Japan .
0789502  12/1980  U.S.S.R. .

OTHER PUBLICATIONS

*Survey of Organic Syntheses,* Buehler et al., Wiley—Interscience, 1974, p. 884.
*Handbook of Chemistry and Physics,* 55th Edition, (1974), CRC Press, Inc., pp. C-76,-80,-411,-336,-32-2,-406.
*Unit Process in Organic Synthesis,* 5th Edition, (1958), P. H. Groggins, McGraw-Hill Book Co. Inc., pp. 770-772.

*Primary Examiner*—Thomas A. Waltz
*Attorney, Agent, or Firm*—L. I. Grim; M. Turken

[57] ABSTRACT

Improvements in efficiencies and yields are achieved in the production of a saturated aliphatic monocarboxylic acid containing 5 to 9 carbon atoms from its corresponding aldehyde by rapidly hydrolyzing the anhydride of the monocarboxylic acid formed in the oxidation. The hydrolysis is accomplished by contacting the anhydride with water at a temperature from about 130° C. to about 215° C. and at a pressure under which the water is maintained in the liquid state to convert the anhydride to its corresponding acid.

10 Claims, 1 Drawing Figure

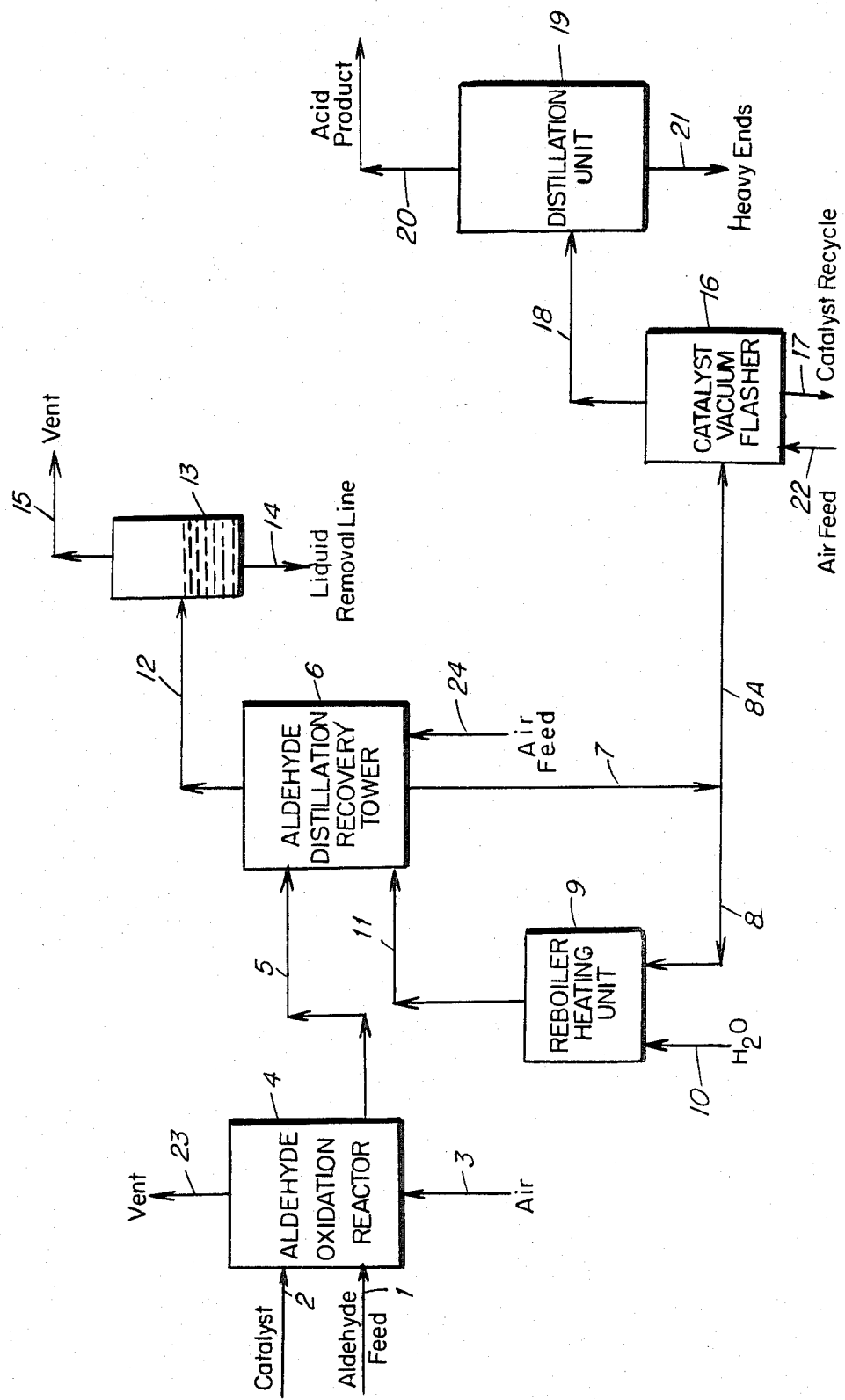

HYDROLYSIS OF ANHYDRIDE IN THE PRODUCTION OF $C_5$-$C_9$ SATURATED ALIPHATIC MONOCARBOXYLIC ACIDS

The present invention relates to a process for improving efficiencies and yields in the production of a saturated aliphatic monocarboxylic acid containing 5 to 9 carbon atoms by the oxidation of its corresponding aldehyde. During the course of the oxidation reaction, anhydrides of the $C_5$-$C_9$ aliphatic saturated monocarboxylic acids are formed and are slowly hydrolyzed to their respective acids at room temperature. In the recovery of the acid product by distillation, the anhydrides present are not recovered with the acid product and can be lost in the heavy ends which are discarded. By this invention, a process is described wherein the anhydrides are rapidly hydrolyzed to the acid product in the acid recovery step by contacting the anhydride with water at elevated temperatures in excess of 130° C. and sufficient pressures to maintain the water in its liquid state.

BACKGROUND OF THE INVENTION

An improved process for the production of a saturated aliphatic monocarboxylic acid containing 6 to 9 carbon atoms by the oxidation of the corresponding aldehyde of the acid in the presence of a catalyst comprising copper and manganese is described in copending application, U.S. Ser. No. 345,890 filed Feb. 4, 1982, now abandoned, and assigned to Celanese Corporation. In another copending application, U.S. Ser. No. 423,899 filed Sept. 27, 1982, now U.S. Pat. No. 4,487,720, and assigned to Celanese Corporation, a further improvement is described in the production of a saturated aliphatic monocarboxylic acid containing 5 to 9 carbon atoms using a one stage oxidation of the corresponding aldehyde to the acid in the presence of a catalyst comprising copper and manganese compounds soluble in the saturated aliphatic monocarboxylic acid. In both of these processes, an anhydride of $C_5$-$C_9$ saturated aliphatic monocarboxylic acid, in an amount from about 1 to about 20 weight percent or higher, of the total reaction product is produced. The anhydride, a by-product of the aldehyde oxidation, can be hydrolyzed completely to the acid in the presence of water at room temperature and atmospheric pressure over an extended period of time such as about 6 hours to about 20 hours or longer. However, the necessity of taking this much time to recover the acids from the anhydride by hydrolysis, or alternatively, the discarding of the anhydride resulting in the complete loss of the corresponding acid, is a serious economic detriment to commercial production of the acids by these processes.

There are various prior art processes for the production of anhydrides from aldehydes wherein hydrolysis of the anhydride is disclosed. However, the anhydrides are considered desirable products in the context of these processes and it is therefore desired to inhibit such anhydride hydrolysis. For example, in U.S. Pat. No. 2,293,104 entitled "Oxidation of Aldehyde" issued to Bludworth Aug. 18, 1942 and the glutaric anhydride process described in U.S. Pat. No. 2,820,821 entitled "Process for Oxidizing Glutaraldehydes" issued to Guest et al Jan. 21, 1958, the hydrolysis of these anhydrides in the presence of water, were found to be rapid at temperatures below 100° C. and considered detrimental to the process. In the production of $C_5$-$C_9$ saturated aliphatic monocarboxylic acid, the by-product anhydride is not desired because it is slow in its hydrolysis at temperatures below 100° C. and rapid means of acid hydrolysis is required.

THE INVENTION

The present invention relates to a process for improving efficiencies and yields in the production of a saturated aliphatic monocarboxylic acid containing 5 to 9 carbon atoms by the oxidation of its corresponding aldehyde. It has been discovered that in the foregoing oxidation process, anhydrides of the $C_5$-$C_9$ saturated aliphatic monocarboxylic acid are formed, and if these anhydrides are not converted or hydrolyzed to their respective acids, the high boiling anhydride components will be discarded with other high boilers in the distillation recovery of the desired acid product thus causing a significant decrease in the efficiency and yield of such product. It has been further discovered that if the anhydrides of the $C_5$-$C_9$ aliphatic saturated monocarboxylic acids are contacted with a sufficient amount of water in the liquid state at temperatures from about 130° C. to about 215° C. and at pressures sufficient to maintain the water in the liquid state, the anhydrides are rapidly hydrolyzed to their respective acids.

The hydrolysis of the acid anhydrides can be conducted in any equipment wherein sufficient pressure can be maintained so that the water will be kept in its liquid state at elevated temperatures. After the hydrolysis occurs, the acid reaction product can be distilled to recover the acid. A preferable technique for the hydrolysis reaction is depicted in the accompanying drawing using a pressurized reboiler heating unit at elevated temperatures.

The drawing schematically depicts a process flow diagram which illustrates the process of this invention.

Air is transmitted via line 3 into an aldehyde oxidation reactor 4, having a vent 23. The reactor 4 contains an aldehyde such as heptanal, fed through line 1 along with the catalysts such as the combination of cupric acetate and manganous acetate, fed through line 2. The effluent from the oxidation reactor 4 comprising an acid product such as heptanoic acid is sent via line 5 to an aldehyde distillation recovery tower 6 containing an air feed 24. The air feed oxidizes the copper catalyst to maintain the copper in its highest oxidized state to prevent the copper from plating on the tower 6. The catalyst-acid product containing anhydride is passed via line 7 to line 8 where a portion of the catalyst acid product is diverted to a pressurized reboiler heating unit 9 which contains a water feed line 10. The reboiler heating unit 9 is operated at a pressure such that the water is maintained in a liquid state and is contacted with the anhydride at a temperature of from about 130° C. to about 215° C. After the hydrolysis has occured, the acid and water are returned to the aldehyde distillation recovery tower 6 via line 11. The unreacted aldehyde and water are distilled overhead and are passed via line 12 to an aldehyde-water decantation unit 13 containing a vent 15 and a liquid removal line 14. The aldehyde is decanted from the water (not shown) and can be removed or recycled to the aldehyde oxidation reactor 4. The remaining portion of the catalyst-acid product in line 7 is passed via line 8A to the catalyst vacuum flasher 16 into which air is fed through line 22 for the purpose of maintaining the copper in its highest oxidized state thus preventing it from plating out. A catalyst solution-containing acid such as heptanoic acid, is removed from flasher 16 through line 17 and can be recycled to the aldehyde reactor 4. The acid product is distilled overhead via line 18 and passed to the distillation unit 19. The finished acid product distilled overhead is recovered through line 20. The heavy ends residue is removed from the system through line 21.

The contact of the liquid water with the anhydride can be carried out at temperatures from about 130° C. to about 215° C., preferably from about 150° C. to about 170° C. at pressures from about 10 psig to about 100 psig or higher, preferably from about 10 psig to about 60 psig.

The amount of water used in the hydrolysis step can range from stoichiometric amounts for the hydrolysis of the anhydride to an excess of 300% or higher to achieve substantially complete hydrolysis of the anhydride.

The invention will be illustrated by the following examples.

EXAMPLE 1

The hydrolysis rate of heptanoic anhydride was determined at 60° C. in a sealed 120 milliliter bottle containing 3 milliliters water (200% stoichiometric excess for the anhydride) and 100 milliliters of heptanoic acid reaction product containing 13.2 weight percent heptanoic anhydride obtained by the liquid oxidation of heptanal in the presence of 300 parts per million each of manganous acetate and cupric acetate. The sealed bottle was placed in a temperature bath at 60° C. and a 10 milliliter sample was withdrawn from the bottle at varying intervals. These samples were analyzed for anhydride content by gas chromatography. The following data were obtained:

TABLE I

| Sample | Time (Minutes) | Anhydride (Wt. %) |
|---|---|---|
| 1 | 0 | 13.2 |
| 2 | 90 | 5.0 |
| 3 | 120 | 3.7 |
| 4 | 180 | 2.0 |
| 5 | 210 | 1.6 |

EXAMPLE 2

A 250 milliliter round bottom flask, fitted with a reflux condenser, was filled to the neck with heptanoic acid reaction product containing 15 weight percent heptanoic anhydride. The contents of the flask were heated to 160° C. and an amount of water, equivalent to 110% of the stoichiometric amount of water necessary to convert the anhydride to the acid, was slowly added through the top of the condenser. The water had to be added slowly to prevent spattering caused by rapid evaporation of the water, and the addition took almost five minutes. The conversion of anhydride to acid appeared to be very rapid and limited only by the addition rate. Analysis of the final flask contents revealed about 1% heptanoic anhydride present. At atmospheric pressure and at 160° C., it is difficult to contact the liquid water with the anhydride to provide the complete hydrolysis of the anhydride.

EXAMPLE 3

Heptanal was converted to heptanoic acid in a liquid phase oxidation reactor in the presence of 300 parts per million each of cupric acetate and manganous according to the procedure described in copending U.S. patent application Ser. No. 345,890 filed Feb. 4, 1982, now abandoned, and U.S. Ser. No. 423,899 filed Sept. 27, 1982, now U.S. Pat. No. 4,487,720, both applications assigned to Celanese Corporation. The reactor product was fed to an aldehyde recycle distillation column, in which air was fed into the base material liquid being distilled to prevent copper from plating on the distillation unit, to recover unconverted heptanal which was recycled to the oxidation unit. The tower bottoms material fed to the aldehyde recycle column contained the manganese and copper catalyst and had the following composition:

| Base Material | Weight % |
|---|---|
| Heptanal | 0.5 |
| Hexanoic acid | 2.2 |
| 2-Methylhexanoic acid | 5.3 |
| Heptanoic acid | 80.5 |
| Hexylhexanoate | 0.7 |
| Hexylheptanoate | 0.9 |
| Heptanoic anhydride | 9.8 |

The above tower bottoms material was fed to a one plate 316 stainless steel distillation column called a "flasher" to separate the acid products and by-products from the catalysts. The flasher contained a reboiler loop used for the forced circulation of reaction product to improve heat transfer and mixing of the reactants. The reboiler loop was fitted with valves allowing for the loop portion to be isolated from the rest of the column and placed under a pressure of 35 psig. Water was added to the reboiler loop under pressure and while being maintained in its liquid state was contacted with the heptanoic anhydride at a temperature of 165° C., resulting in the rapid hydrolysis of the anhydride. After the hydrolysis of the anhydride to its acid, the contents of the reboiler loop reentered the flasher column and the water flashed overhead along with the acid products and by-products. The base material feed rate to the flasher was 21 kilograms per hour, the water addition rate to the forced circulation loop was 2.2 to 5.0 milliliters per minute depending on the amount of water to be used for hydrolysis, and the forced circulation loop residence time was one second. A sufficient amount of air was added to the flasher to prevent copper from plating on the equipment during distillation. The tower bottoms taken off of the high boilers and catalyst to be recycled back to the oxidation unit was 3 kilograms per hour. Overhead pressure of the flasher was 60 millimeters mercury.

Heptanoic anhydride hydrolysis was accomplished under the above conditions yielding the following results:

| Percent of stoichiometric water added for heptanoic anhydride hydrolysis | 85% | 133% | 200% |
|---|---|---|---|
| Anhydride conversion to acid | 85% | 90% | 84% |

A residence time longer than one second in the reboiler loop for the 133% and 200% stoichiometric excess of water will result in substantially complete conversion of the anhydride.

It should be readily apparent that the hydrolysis described in Example 3 is very fast (one second) for 85–90% anhydride conversion at 165° C. and a pressure of 35 psig compared to 3.5 hours for Example 1 at 60° C. and 5 minutes for Example 2 at atmospheric pressure and 160° C.

The anhydride can be hydrolyzed to its corresponding acid in the aldehyde recycle recovery column as indicated in the accompanying drawing. The column contains a forced circulation reboiler loop wherein the water would be added under pressure (to maintain it in the liquid state at temperatures above the boiling point of water) to the reboiler loop for the anhydride hydrolysis conversion. The aldehyde recovery column is operated under reduced pressure so that the water coming out of the reboiler loop will be flashed from the acid along with the aldehyde. Since the aldehyde is insoluble in water, the recovery of the heptanal and water will be collected in a two-phase liquid medium. The aldehyde can be readily separated by the decantation from the water and recycled back to the oxidation unit while the water, if desired, can be recycled to the forced circulation reboiler loop for hydrolysis of the anhydride.

What is claimed is:

1. In a catalytic process for oxidizing an organic saturated aliphatic aldehyde containing from 5 to 9 carbon atoms to its corresponding organic saturated monocarboxylic acid wherein the catalyst is a combination of manganese and copper compounds soluble in said monocarboxylic acid, the improvement comprising hydrolyzing the anhydride of said monocarboxylic acid formed in said oxidation by contacting said anhydride with a sufficient amount of water at a temperature from about 130° C. to about 215° C. and a pressure under which the water is maintained in the liquid state for a period of time sufficient to convert said anhydride to is corresponding acid.

2. The process of claim 1 wherein the hydrolysis is carried out at a pressure of from about 10 psig to about 100 psig.

3. The process of claim 1 wherein the pressure of the hydrolysis is from about 10 psig to about 60 psig.

4. The process of claim 1 wherein the temperature of the hydrolysis is from about 150° C. to about 170° C.

5. The process of claim 3 wherein the anhydride is valeric anhydride.

6. The process of claim 3 wherein the anhydride is heptanoic anhydride.

7. The process of claim 3 wherein the anhydride is nonanoic anhydride.

8. The process of claim 1 wherein the hydrolysis temperature is about 150° C. to about 170° C., the hydrolysis pressure is from about 10 psig to about 60 psig and the anhydride is valeric anhydride.

9. The process of claim 8 wherein the anhydride is heptanoic anhydride.

10. The process of claim 8 wherein the anhydride is nonanoic anhydride.

* * * * *